US006183733B1

(12) United States Patent
McKibben

(10) Patent No.: US 6,183,733 B1
(45) Date of Patent: Feb. 6, 2001

(54) COMPOSITIONS AND METHODS OF ATTRACTING OVERWINTERING BOLL WEEVILS

(75) Inventor: Gerald H. McKibben, Starkville, MS (US)

(73) Assignee: Cotton Incorporated, New York, NY (US)

( * ) Notice: Under 35 U.S.C. 154(b), the term of this patent shall be extended for 0 days.

(21) Appl. No.: 09/289,910

(22) Filed: Apr. 13, 1999

(51) Int. Cl.[7] .......................... A01N 31/04; A01N 35/02; A01N 27/00; A01N 31/16; A01N 57/00; A01N 25/00; A01N 63/00; A01M 1/10

(52) U.S. Cl. ........................ 424/84; 424/93.1; 424/93.46; 424/93.5; 424/195.1; 424/405; 424/409; 514/84; 514/122; 514/132; 514/703; 514/720; 514/729; 514/762; 514/951; 43/107; 43/132.1

(58) Field of Search .............................. 424/84, 405, 409, 424/93.1, 93.461, 93.5, 195.1; 514/703, 720, 729, 951, 953, 84, 122, 132, 762; 43/107, 132.1

(56) References Cited

U.S. PATENT DOCUMENTS

| | | | |
|---|---|---|---|
| 3,808,303 | 4/1974 | McKibben | 264/41 |
| 3,954,968 | 5/1976 | McKibben et al. | 424/84 |
| 4,027,420 | 6/1977 | McKibben et al. | 43/124 |
| 5,290,556 | 3/1994 | McKibben et al. | 424/405 |
| 5,413,784 | 5/1995 | Wright et al. | 424/93.5 |

OTHER PUBLICATIONS

Hedin, P.A. et al., "Identification and Field Evaluation of the Compounds Comprising the Sex Pheromone of the Female Boll Weevil," Journal of Chemical Ecology, vol. 5, No. 4, 1979, pp. 617–627.*

Bottrell, D. G., et al., "Overwinterning habiotats of the boll weevil in the Rolling Plains of Texas", *Environ. Entomol.*, 1(5) 633–638, 1972.

Chang, J. F., et al., "Attractiveness oc cotton volatiles and grandlure to boll weevils in the field", Proceedings Beltwide Cotton Production Research Conferences, 102–104, 1987.

Dickens, J. C., "Greenleaf volatiles enhance aggregation pheromone of boll weevil", *Anthonomous grandis. Entomologia Experimentalis et Applicata*, 52(3): 191–203, 1989.

Gueldner, R. C., et al., "Constituents of the Cotton Bud. XIX. Attractancy to the Boll Weevil of the Terpenoids and Related plant Constituents", *J. Econ. Entomol.*, 63(6): 1819–1821, 1970.

McKibben. G.H., et al., "Development of the Bait Principle for Control of Boll Weevils: Addition of Terpenoids and Related Plant Constituents", *J. Econ. Entomol.*,64(6): 1493–95, 1971.

McKibben, G. H., et al., "Boll weevils are attracted to volatile oils from cotton plants", *Environ. Entomol.*, 6(6): 804–806. 1977.

Minyard, J. P., et al., "Constituents of the cotton bud: Compounds attractive to the boll weevil", *J. Agr. Food Chem.*, 17(5): 1093–1097, 1969.

Rummel, D. R., et al., "A wild feeding host of the boll weevil in West Texas", *Southwest. Entomol*, 8: 101–106, 1978.

Thompson, A. C., et al., "Consntituents of the Cotton Bud. XVI. The Attractance Response of the Boll Weevil to the Essentials Oils of a Group of Host and Nonhost Plants", *J. Econ. Entomol.*, 63(3): 751–753, 1970.

Viehoever, A., et al., "Chemistry of the cotton plant with special reference to upland cotton", *J. Agric. Res.*, 13: 345–52, 1918.

* cited by examiner

*Primary Examiner*—John Pak
(74) *Attorney, Agent, or Firm*—Burns, Doane, Swecker & Mathis L.L.P.

(57) ABSTRACT

Compositions and methods for attracting, killing, and/or neutering populations of boll weevils and other insects which spend the winter in areas with thick vegetation are disclosed. With respect to boll weevils, certain plant compounds, when presented along with Grandlure, the synthetic pheromone of the cotton boll weevil (*Anthonomus grandis* Boh.), increase the capture of boll weevils by as much as 50% as compared to Grandlure alone. The compounds, beta-caryophyllene, eugenol and myrcene, are among those present in leaves in overwintering sites favored by boll weevils. With respect to controlling boll weevil populations, the compounds can be used alone, in combination with Grandlure, and/or in combination with compounds which are toxic to boll weevils or which inhibit their ability to develop normally or reproduce. With respect to controlling other overwintering insects, appropriate compounds can be identified from the leaf litter surrounding their overwintering sites, and pheromones for the insects are generally known. The compounds can be used in traps, or formulated into polymeric controlled release formulations, along with the Grandlure and/or toxicants, insect growth regulators or insect sterilants.

25 Claims, No Drawings

COMPOSITIONS AND METHODS OF ATTRACTING OVERWINTERING BOLL WEEVILS

FIELD OF THE INVENTION

This invention relates to control of boll weevils and other insects which overwinter in areas with thick vegetation, particularly to attracting these insects and optionally killing them or rendering them infertile.

BACKGROUND OF THE INVENTION

Boll weevils are insects found in North, Central and South America which feed on cotton plants, causing serious damage to the plants and reducing harvest yield. Boll weevils develop through egg, larvae, pupae, and adult stages.

All life stages except the adult stage are spent inside cotton squares or bolls. Male boll weevils release an aggregating pheromone after feeding on cotton squares, and both males and females are attracted to this pheromone. Adult, overwintered females feed for 3 to 7 days, mate, and start laying eggs. Starting in the spring, females lay one egg per square or several in a boll. Each female usually lays an average of 150 eggs in her lifetime, each of which hatch in about three to five days. The resulting grubs or larvae feed about a week inside squares or bolls before changing into pupae; this stage lasts three to five days. Adults develop from pupae and cut their way out of squares or bolls. New adults feed from three to five days, mate, and begin laying eggs. These cycles are repeated during the season until the cotton plants are either destroyed or killed by frost. It is estimated that a single pair of weevils can generate up to two million offspring per year.

Numerous attempts have been made to trap, kill or destroy boll weevils. Farmers will often defoliate their crops to kill the weevils or at least remove their food source, and/or apply pesticides or insecticides over the crops to kill them. The insecticides are typically applied before pin-head square (before the cotton squares are one-third grown), so the weevils are killed before reproduction occurs.

The use of insecticides is associated with a variety of problems, including toxicity to humans and animals, and the relatively long half-life of a variety of insecticides. The chemicals can cause environmental pollution and also present health concerns for humans and animals which come into contact with the insecticides. Further, the chemicals often kill a variety of beneficial insects, including parasitic wasps, ladybugs and other insects that prey on the tobacco budwormn and other caterpillars that attack cotton.

There are currently eradication programs in at least seven states in the United States, and control and/or containment programs are being carried out in Mexico and every country in Central and South America where cotton is grown commercially. The eradication programs use various traps to attract and kill the boll weevils. The traps typically include Grandlure, a four-component mixture which functions as a synthetic pheromone for the boll weevil. In states where the boll weevil has been eradicated, pheromone-baited traps are used for survey purposes, to detect any new re-infestations. Use of the pheromone allows one to minimize the amount of insecticide used to kill the boll weevils, and to place the insecticide in a controlled location rather than broadly over an entire cotton field.

Examples of boll weevil attractant compositions including Grandlure are described, for example, in U.S. Pat. No. 3,803,303. Grandlure has been used in combination with feeding stimulants, poisons and other compounds, in a variety of different types of devices, for example, those described in U.S. Pat. No. 4,027,420. Polymeric compositions for attracting boll weevils using a sex attractant in combination with polyethylene glycol and a toxicant such as p-dichlorobenzene are disclosed, for example, in U.S. Pat. No. 3,803,303. The contents of these patents is hereby incorporated by reference. Plant attractants such as caryophylline oxide and beta-bisabalol have been used in some of these devices, where the attractant is applied to cotton dental-rolls. Other controlled-release dispensers have been developed to give long-term release of Grandlure (McKibben and Davich, Environmental Entomology, 6(6) :804–806 (1977). Volatile compounds present in the cotton plant have been shown to attract boll weevils, although not when they are diapausing.

In the wintertime, boll weevils undergo certain physiological changes (entering a state of diapause) so that they can go without food during hibernation and survive the winter. Major changes in the boll weevil's body include accumulation of excess body fat, a reduction in water content, and cessation of reproduction. Diapausing boll weevils typically spend the winter near cotton fields, in woody areas, along ditch banks, and around trash and litter areas of cotton gins and old farm buildings. Development of diapausing weevils in fields usually continues until food supplies are destroyed, either by a killing frost or by defoliation and stalk destruction. Weevils entering diapause have been found as early as July; however, peak development of diapause usually coincides with the maturity of cotton plants.

Diapausing boll weevils are not as attracted to Grandlure as are reproductive boll weevils, so the traps are not effective at attracting and killing diapausing boll weevils. One method for controlling the population of diapausing boll weevils is defoliation. Defoliation is not necessary for effective diapause control, but defoliation enhances effectiveness of control by reducing food and breeding sites for later development of weevils. Typically, defoliants are applied within 10 to 14 days after the last application of an insecticide, or an insecticide such as methyl parathion, Guthion, malathion and/or various pyrethroids, is added to the defoliants. Since the cotton stalks are also a food source for the boll weevil, they are also typically destroyed.

In the summertime, male boll weevils produce enough of their pheromone that it competes with the traps, lessening their effectiveness. Accordingly, the eradication programs do not typically use the traps in the summer months.

It would be advantageous to provide compositions, devices and methods for attracting boll weevils and killing them or rendering them infertile year round, including in the winter when they are in a state of diapause, and in the summer, when the natural pheromone secreted by the male boll weevils competes with the Grandlure-baited traps.

Similar problems are also observed with respect to other insects which overwinter in areas with thick vegetation. It would also be useful to provide compositions, devices and methods for attracting these insects and optionally killing them or rendering them infertile. The present invention provides such compositions, devices and methods.

SUMMARY OF THE INVENTION

Compositions, devices and methods for attracting insect populations which overwinter in areas with thick vegetation, in particular, boll weevil populations, and optionally killing or rendering the populations infertile, are disclosed. With respect to the boll weevil, the compositions include a pheromone for boll weevils, preferably Grandlure, and also include eugenol, beta-caryophyllene and/or myrcene. Compositions including one or more of these components can be used year-round as attractants for boll weevils. With respect to other insect populations, the compositions include volatile plant extracts from leaves found in areas in which the insects overwinter and which attract the insects, and pheromones for the particular insects.

The compositions can include additional components. These components include attractants other than plant volatiles, insecticides, insect growth regulators, and insect sterilants. Suitable insecticides effective at killing boll weevils and other overwintering insects are well known to those of skill in the art, and include organophosphates, carbamates and pyrethroids. Malathion, Guthion and methyl parathion are preferred insecticides. Cottonseed oil is an example of a suitable boll weevil attractant. Dimilin is an example of a suitable insect growth regulator.

The compositions can be used in traps such as those commonly used to attract boll weevils or other overwintering insects. Such traps are well known to those of skill in the art, and are commonly used in many states in their boll weevil eradication programs.

In one embodiment, the compositions are included in polymer-based insecticidal compositions which are impervious to environmental conditions. Such compositions typically include a polymer, the compositions and an insecticide, and optionally include one or more attractants in addition to the plant volatiles. The devices can be in the form of solid pellets and hollow tubes that are filled or partially filled with the compositions described herein.

The devices can be used to attract and kill boll weevils, or to monitor cotton fields in which the boll weevil population has purportedly been eradicated. Generally, the traps or polymeric compositions are set out in or around a cotton field, and the boll weevils are attracted to the traps and/or polymeric compositions and killed.

DETAILED DESCRIPTION OF THE INVENTION

Compositions, devices and methods for attracting insect populations which overwinter in areas with thick vegetation, in particular, boll weevil populations, and optionally killing or rendering the populations infertile, are disclosed.

With respect to boll weevils, the compositions are effective at attracting boll weevils when they are in various physiological stages of diapause and are not as strongly attracted to the synthetic pheromone Grandlure as they are in their reproductive stages, and also in the summertime when male boll weevils produce enough natural pheromone to compete with the Grandlure-baited traps commonly used in boll weevil eradication programs.

In the wintertime, insects such as the boll weevil hibernate on the ground in leaf litter and other plant debris, and the dead plant material insulates boll weevils from the cold. Selection of an appropriate habitat is crucial for the boll weevil to survive a harsh winter. It is believed that once a male boll weevil finds an appropriate location, he emits a pheromone to attract other boll weevils to the location.

Applicant evaluated numerous volatile compounds present in the dead plant material as well as volatile compounds present in leaves of plants common in overwintering areas, and determined that selected volatile compounds found in the leaves of the plants common to the overwintering areas attract the boll weevil. The compounds were somewhat active by themselves in attracting boll weevils. However, when combined with Grandlure, the resulting compositions were more effective at attracting boll weevils than Grandlure alone, the compounds alone, or the additive effectiveness of the compounds. The combination appears to mimic the combination of volatile compounds a boll weevil would follow to find an appropriate overwintering location.

Accordingly, while it is uncertain how long the active compounds remain in the leaves after falling to the ground, and while not wishing to be bound by a particular theory, it is believed that the boll weevils are attracted to the composition in a similar manner to how they select favorable overwintering habitats. It is further believed that the compositions provide a synergistic effect, rather than an additive effect. However, an additive effect alone would represent a significant improvement in the control of boll weevil populations, since the relatively inexpensive plant volatiles could replace, in part, the relatively expensive Grandlure.

The most active volatile components of leaves found in overwintering sites for the boll weevil appear to be eugenol, beta-caryophyllene, and myrcene. Compositions including one or more of these components can be used year-round as attractants for boll weevils, for example, in containment and/or control applications.

The compositions and methods described herein can be used in an effective diapause control program for boll weevil populations. An effective diapause control program can lessen the total number of insecticide applications needed in the following season for maximum protection from boll weevils, minimize the destruction of beneficial insects that suppress bollworms, spider mites, and other harmful insects, minimize the risk of weather interfering with control measures and reducing the effectiveness of control measures, and create favorable conditions for eliminating weevils as pests of economic importance.

As applied to other overwintering insect populations, the plant volatiles useful for attracting these insects can be identified, for example, using the criteria described in Example 1. Pheromones for many of these insects are known.

I. Compositions

A. Plant Volatiles

With respect to controlling boll weevil populations, the compositions include eugenol, beta-caryophyllene, and/or myrcene, preferably in an amount effective to attract overwintering boll weevils. These compounds are commercially available, and can be synthesized using known chemistry. Derivatives of these volatiles can also be used, including alkylated derivatives and halogenated derivatives. An example of a suitable alkylated derivative is methyl eugenol. Any of the many terpenoid compounds that make up the essential oils in green leafy plants will likely have the ability to attract boll weevils and other insects to varying degrees. Such derivatives can be readily synthesized using known chemistry.

Depending on the overwintering site and the type of insect whose population is to be controlled, other plant volatiles can be effective. Those of skill in the art can determine an appropriate plant volatile by extracting the leaf litter in a particular overwintering site, separating the individual components, for example, by column chromatography, and evaluating the attractant ability of the compounds, alone or in combination with Grandlure or other suitable pheromones, for example, following the procedures in Example 1 below.

B. Pheromones

With respect to the boll weevil, the compositions preferably also include an effective, boll weevil attracting amount of Grandlure or an effective analogue thereof, or the natural boll weevil pheromone. With respect to other overwintering insects, pheromones for many insects are known or can be readily identified.

Grandlure is a synthetic boll weevil pheromone, and is extremely effective at attracting boll weevils. Grandlure is known to be effective at doses of approximately 10 mg of Grandlure per trap every 14 days. As the weevil population is reduced, the pheromone becomes increasingly effective at "calling" weevils to the trap. Continuous trapping helps determine the treatment efficacy.

An effective amount of the plant volatiles and the Grandlure depends on several factors, such as the size of the cotton fields the boll weevils may be infesting, the size of the overwintering habitat, the particular season the trap is set, the degree of infestation, and the like. Those of skill in the art, taking these and other factors into consideration, can readily determine an appropriate amount of the components to achieve effective control of a particular boll weevil population.

C. Insecticides

Any insecticide known to be effective at killing boll weevils or other overwintering insects can be used. Suitable insecticides effective at killing these insect populations are well known to those of skill in the art, and include organophosphates, carbamates and pyrethroids. Preferred insecticides are those which are approved by the Environmental Protection Agency as environmentally safe for the particular end use, for example, in the case of boll weevils, for use on cotton. Also, it is preferred to use only short-lived materials that will not carry over in the soil from one season to the next. Malathion, Guthion, methyl parathion and any of the various pyrethroid compounds which are commercially available are preferred insecticides, with malathion currently being the most preferred insecticide.

Some biological insecticides are known which are effective at killing the boll weevil, and biological insecticides are also known for a variety of other overwintering insect populations. Examples include the B. thuringiensis microbe given the designation strain San Diego. The spores or crystals of this microbe are useful to control the cotton boll weevil. U.S. Pat. No. 5,413,784 describes a useful biopesticide with activity against the boll weevil. The biopesticide is an entomopathogenic fungus, *Beauveria bassiana*, preferably *Beauveria bassiana*, ATCC-74040 (ARSEF-3097). By using the microbe or fungus, or mutants thereof, boll weevils can be controlled without the environmental and public safety hazards presented by chemical control agents.

D. Optional Components

The compositions can include additional optional components. These components include attractants other than the plant volatiles and the pheromones, insect growth regulators, and insect sterilants.

Cottonseed oil is an example of a suitable attractant for boll weevils. In one embodiment the composition is in the form of an oil in water emulsion which includes cottonseed oil, water, an emulsifying agent, Grandlure, the plant volatiles, and an insecticide. The compositions also preferably include a preservative such as potassium sorbate, BHA, BHT, and/or the methyl ester of parahydroxybenzoic acid. The cottonseed oil can be thickened with pyrogenic silica, glycerol, cellulose and/or polysaccharide gum-type organic thickeners such as hydroxy ethyl cellulose and locust bean gum. Suitable emulsifying agents include polyoxyethylene sorbitan monooleate and sorbitan monooleate.

Insect growth regulators are compounds, either natural or synthetic, which influence insect growth and development (e.g., affecting boll weevil grub integument formation during shed, resulting in deformed pupae and adults or premature death.) Dimilin is an example of a suitable insect growth regulator for boll weevils.

II. Traps including the compositions

The compositions can be used in traps such as those commonly used to attract boll weevils. Such traps are well known to those of skill in the art, and are commonly used in many states in their boll weevil eradication programs.

The traps are typically plastic, yellow-green fluorescent traps that are highly visible around cotton fields. The color of the trap is effective at attracting boll weevils, in addition to the compositions placed inside the traps.

In one embodiment, the trap is an inverted cup, topped with a cone-shaped wire mesh screen. A capture chamber on top of the cone contains a dispenser for the boll weevil attractant composition. A chip with insecticide can be added to prevent weevils from escaping.

Preferably, the boll weevil trap includes a support means, colored or painted daylight fluorescent yellow, an open-ended hollow guiding means mounted on the upper end of the support means, with a perforated hollow trapping means detachably affixed at its open lower end to about the open upper end of the guiding means. The guiding means is adapted to be releaseably affixed to the upper end of the support means to provide an annular space between the outside of the support means and the inside of the open lower end of the guiding means. The opening at the upper end of the guiding means is substantially smaller than the opening at the lower end of the guiding means, and the opening at the upper end of the guiding means extends within the interior space of the trapping means.

The trap can be placed in a location where boll weevils may be present, and when the trap includes an effective amount of the compositions described herein, boll weevils are attracted to the trap. The boll weevils are attracted by the combination of the daylight fluorescent yellow color of the trap and the compositions described herein, and move positively geotropically upwardly on the trap into a perforated collecting or trapping means at the upper location or end of the trap.

Initially these traps may be placed from 100 to 250 feet apart around the edge of a cotton field. After eradication, the cotton fields can be monitored, for example, with 1 trap for every 10 acres.

Those of skill in the art can readily adapt the boll weevil traps for use in controlling populations of other overwintering insects.

III. Polymer-based insecticidal compositions

In one embodiment, the compositions are included in polymer-based insecticidal compositions which are impervious to environmental conditions. Such compositions typically include a polymer, a plant volatile such as myrcene, eugenol and/or beta-caryophyllene, Grandlure or an equivalent pheromone, and an insecticide, and optionally include one or more attractants. The devices are typically in the form of solid pellets or hollow tubes that are filled or partially filled with the compositions described herein.

Suitable polymers for use in preparing the polymer-based insecticidal compositions can include one or more of the following moieties: acrylates, chlorinated diphenyls, alkyds, chlorinated rubbers, allyl groups, aniline-formaldehyde adducts, coumarone-indene adducts, aramid groups, cyclohexanone-formaldehyde adducts, epoxy groups, epichlorhydrin groups, bisphenol moieties, formaldehyde-sulfonamide adducts, phenol-aldehyde adducts, phenol-copal reaction products, sulfonamide-aldehyde adducts, and urea- (form)aldehyde adducts. Examples of suitable polymers for use in preparing the compositions include celluloses such as cellulose, methylcellulose, ethyl cellulose, cellulose acetate, cellulose acetate-butyrate, cellulose acetate-propionate, and cellulose propionate; proteins such as casein; furane, fluorocarbon-based polymers, hydrogenated rosins, lignins, melamine, polyurethanes, vinyl polymers such as polyvinyl acetate (PVAC), polycarbonates, polyvinylidene dinitrile, polyamides, polyvinyl alcohol (PVA), polyamide-aldehyde, polyvinyl aldehyde, polyesters, polyvinyl chloride (PVC), polyethylenes, polystyrenes, polyvinylidene, rubber hydrochloride and silicones.

In one embodiment, a plastisol is prepared from a powdered polymer, for example, a PVC polymer, mixed with crude cottonseed oil as a plasticizer. The cottonseed oil also includes the Grandlure and the plant volatiles. Pellets can be prepared from the plastisol, for example, by dip molding, extrusion, and other means known to those of skill in the art.

In the dip molding process, dip molds are heated to a temperature sufficient to provide full curing of the PVC to form an inner core. Typical temperatures are between 170 and 180° C., to provide a durable support structure and to provide for a controlled release of the pheromone and the plant volatiles. After dipping, the resulting tubular structure can be cured in an oven at a temperature just high enough to achieve a solid, non-tacky surface but low enough to provide a friable surface that insects can chew and ingest. Alternative designs include microspheres and solid cast pellets that are used in a manner similar to the hollow tubes. One advantage in a solid pellet is that mass production is possible by extruding and cutting to the desired length.

In one embodiment, the hollow tubes are prepared from materials that do not necessarily include the Grandlure or the plant volatiles, but are filled with a liquid or gelled bait mixture that includes the Grandlure and the plant volatiles. In this embodiment, heat-sensitive materials can be used that would be destroyed or driven off by the heat treatment used to cure the PVC. Examples of such materials include biological control agents such as Bacillus thuringiensis spores and other biopesticides. Insecticides incorporated into the plastisol kill the boll weevils that ingest it. The pellets when applied in the field attract and induce insects to ingest particles of the pellets. Subsequently, the insects die or are rendered infertile, if insect growth regulators are used. The polymeric devices described herein have the advantages of minimizing the amount of insecticides released into the environment, are species specific, and eliminate the need for constant insecticide reapplication.

The pellets can also be used in laboratory bioassays to determine compounds which are useful for attracting and killing boll weevils. Insects induced to feed are killed. In some formulations, the pellets kill boll weevils that merely remain in contact with the pellets for a given period of time, regardless of whether they fed or not. The pellets can be placed into cages containing boll weevils, and the cages placed in a dark environment overnight at 29° C. Feeding response can be determined by totaling the number of feeding punctures within the bait pellets. Control pellets which do not contain either the Grandlure and/or the plant volatiles do not elicit an attraction or feeding response. Plant volatiles and pheromones specific for other overwintering insects can also be placed in the polymer-based insecticidal formulations described above.

IV. Methods of controlling boll weevil populations using the compositions

The traps as described herein can be set at any time of the year. Those of skill in the art can readily determine an appropriate amount of the compositions to use in a particular trap, and can also determine an appropriate density of traps/acre of cotton field to be protected.

Of course, other commonly used farming practices can also be used to limit early and late food sources for the weevil. These include using later planting dates, selecting early maturing cotton varieties, harvesting early, and destroying the cotton stalks immediately after harvesting. These additional practices will help optimize the effectiveness of the traps at controlling the boll weevil population. Any and all of these steps can and are preferably taken in addition to using the traps as described herein.

The methods can readily be adapted for use in controlling insect populations other than boll weevils.

V. Methods of monitoring cotton fields for boll weevil infestation

When a field is not actually known to be infested with boll weevils, the traps can be placed throughout the area to monitor infestation, typically in a concentration of about 1 trap per 10 acres. If the trap yields a significant number of dead boll weevils, higher concentrations of traps/acre may be required. This embodiment is particular advantageous over the use of Grandlure traps, since the traps otherwise lose their effectiveness when the weevils are diapausing.

The invention will be further understood with reference to the following non-limiting examples.

EXAMPLE 1

Response of dispersing boll weevils to Grandlure plus synthetic plant components A study was done in Coahoma and Quitman counties in Mississippi in which traps were baited with Grandlure using the standard 10 mg dispensers used in the boll weevil eradication programs. Three synthetic plant components were chosen from a larger group of compounds from preliminary field data that showed dispersing boll weevil response to the compounds. The synthetic plant materials were prepared for field tests in traps by applying 40 mg of the oil to ¼ inch by 1 inch cotton dental rolls. Statistical analysis was done using the Least Squares means separations from the SAS GLM procedure. The results are shown below in Table 1.

TABLE 1

Average number of boll weevils captures/trap/day

| Treatment | Capture | P > T |
|---|---|---|
| Grandlure alone | 24 | — |
| Grandlure + beta-caryophyllene | 37 | 0.25 |
| Grandlure + myrcene | 47 | 0.05 |
| Grandlure + eugenol | 50 | 0.03 |

LS Means from SAS GLM procedure; P > F 0.06, 7.69 df. TProb. values compared with blank Accordingly, two compounds, when used with Grandlure, significantly improved the trap captures. Earlier, preliminary tests with the compounds indicated a weak response without Grandlure. The apparent synergistic action of eugenol in this test is believed to be the first instance of a compound not found in the cotton plant or related species acting synergistically with Grandlure.

EXAMPLE 2

Controlled Release Formulation of Grandlure and Beta-Caryophyllene

Three controlled release dispensers were prepared by adding 2.3 g caryophyllene to a 3 ml vial, adding 33 mg vegetable oil, and inserting a ¼ inch by 1 inch cotton dental roll. Five-day capture totals taken in the month of May (when boll weevils are emerging from hibernation quarters) for three repetitions were 141 for Grandlure alone versus 330 for Grandlure plus a caryophyllene dispenser. The difference represents a 230% increase in capture over Grandlure alone, which demonstrates the attractiveness of caryophyllene to overwintered boll weevils.

EXAMPLE 3

Compositions including Grandlure and Beta-Caryophyllene, Eugenol or Myrcene

Non-controlled release dispensers of three plant compounds, beta caryophyllene, eugenol and myrcene, were prepared by pipetting 26 ml of each compound into a cotton dental roll. Five-day capture totals taken when boll weevils were in their overwintering phase were 40 for Grandlure alone versus 56 for Grandlure plus caryophyllene, 58 for Grandlure plus eugenol, and 48 for Grandlure plus myrcene. Statistical analysis (SAS, GLM LSMEANS) showed that both caryophyllene and eugenol, along with Grandlure, captured significantly more boll weevils than Grandlure alone, which demonstrates the attractiveness of caryophyllene and eugenol to overwintered boll weevils.

The invention as described by the specific embodiments is not meant to limit its scope. It is envisioned and apparent that many alternatives and variations may be encompassed by the present invention. It is intended that the spirit and scope of this disclosure include such alternatives and variations.

I claim:

1. A composition for attracting boll weevils comprising an effective, boll-weevil attracting amount of a combination of Grandlure and eugenol.

2. The composition of claim 1, further comprising an insecticide effective at killing boll weevils.

3. The composition of claim 2, wherein the insecticide is selected from the group consisting of malathion, Guthion, and methyl parathion.

4. The composition of claim 2, wherein the insecticide is selected from the group consisting of microbes and fungi effective at killing boll weevils.

5. The composition of claim 1, further comprising a boll weevil attractant other than plant volatiles.

6. The composition of claim 5, wherein the attractant is cottonseed oil.

7. The composition of claim 1, further comprising an insect growth regulator or insect sterilant.

8. A trap for catching boll weevils, comprising an inverted cup topped with a cone-shaped wire mesh screen, with a capture chamber on top of the cone which includes a dispenser for the composition of claim 1.

9. A method for controlling boll weevil comprising: a) administering to a predetermined site an effective boll weevil controlling amount of the composition of claim 1.

10. A plastisol composition for attracting boll weevil comprising: a) a polymer b) Grandlure c) eugenol and d) a plasticizer.

11. The composition of claim 10, further comprising an insecticide.

12. The composition of claim 10, further comprising an insect growth regulator.

13. The composition of claim 10, wherein the polymer is polyvinyl chloride.

14. A composition for attracting boll weevills comprising a polymer, Gradlure and eugenol in the form of pellets, microspheres or tulbules.

15. A composition for attracting boll weevils consisting essentially of an effective, boll-weevil attracting amount of a combination of Grandlure and myrcene.

16. A trap for catching boll weevils, comprising an inverted cup topped with a cone-shaped wire mesh screen, with a capture chamber on top of the cone which includes a dispenser for the composition of claim 15.

17. A method for controlling boll weevil comprising: a) administering to a predetermined site effective boll weevil controlling amount of the composition of claim 15.

18. A composition for attracting boll weevils consisting essentially of an effective, boll-weevil attracting amount of a combination of Grandlure and myrcene, and an additional component selected from the group consisting of a boll weevil attractant other than plant volatiles, an insect growth regulator, an insect sterilant, and an insecticide effective at killing boll weevils.

19. The composition of claim 18, wherein the insecticide is selected from the group consisting of malathion, Guthion, and methyl parathion.

20. The composition of claim 18, wherein the insecticide is selected from the group consisting of microbes and fungi effective at killing boll weevils.

21. The composition of claim 18, wherein the attractant other than plant volatiles is cottonseed oil.

22. A plastisol composition for attracting boll weevils consisting essentially of: a) a polymer b) Grandlure c) myrcene and d) a plasticizer.

23. The composition of claim 22, wherein the polymer is polyvinyl chloride.

24. A composition for attracting boll weevils consisting essentially of a) a polymer b) Grandlure c) myrcene d) plasticizer and e) an additional component selected from the group consisting of an insect growth regulator and an insecticide.

25. A composition for attracting boll weevils consisting essentially of a polymer, Grandlure and myrcene in the form of pellets, microspheres or tubules.

* * * * *

UNITED STATES PATENT AND TRADEMARK OFFICE
CERTIFICATE OF CORRECTION

PATENT NO.    : 6,183,733 B1                                      Page 1 of 1
DATED         : February 6, 2001
INVENTOR(S)   : Gerald H. McKibben It is certified that error appears in the above-identified patent and that said Letters Patent is hereby corrected as shown below:

Title page,
Bottrell reference, delete "Overwinterning" and insert therefor -- Overwintering --;
Chang reference, delete "oc" and insert therefor -- of --;
Gueldner reference, delete "plant" and insert therefor -- Plant --;
Thompson reference, delete "Consntituents" and insert therefor -- Constituents --"
Thompson reference, delete "Essentials" and insert therefor -- Essential --;

Column 10,
Claim 14, delete "tulbules" and insert therefor -- tubules --.

Signed and Sealed this

Sixth Day of November, 2001

*Attest:*

*Attesting Officer*

NICHOLAS P. GODICI
*Acting Director of the United States Patent and Trademark Office*